US007008375B2

(12) United States Patent
Weisel (10) Patent No.: US 7,008,375 B2
(45) Date of Patent: Mar. 7, 2006

(54) ARTICULATING SHAFT

(75) Inventor: Thomas Weisel, Ventura, CA (US)

(73) Assignee: Surgical Solutions LLC, Valencia, CA (US)

( * ) Notice: Subject to any disclaimer, the term of this patent is extended or adjusted under 35 U.S.C. 154(b) by 35 days.

(21) Appl. No.: 10/816,341

(22) Filed: Mar. 31, 2004

(65) Prior Publication Data
US 2004/0199051 A1 Oct. 7, 2004

Related U.S. Application Data

(60) Provisional application No. 60/460,487, filed on Apr. 3, 2003.

(51) Int. Cl.
*A61B 1/00* (2006.01)
(52) U.S. Cl. .................. 600/141; 600/139; 600/142
(58) Field of Classification Search ........ 600/139–152; 138/118, 137; 606/170; 604/280–282, 95, 604/264
See application file for complete search history.

(56) References Cited

U.S. PATENT DOCUMENTS

| | | | |
|---|---|---|---|
| 3,470,876 A | 10/1969 | Barchilon | |
| 3,605,725 A | 9/1971 | Squiers | |
| 4,483,562 A | 11/1984 | Schoolman | |
| 4,662,371 A | 5/1987 | Whipple et al. | |
| 4,763,669 A | 8/1988 | Jaeger | |
| 4,790,294 A * | 12/1988 | Allred et al. | 600/141 |
| 4,834,069 A | 5/1989 | Umeda | |
| 4,880,115 A | 11/1989 | Chaussadas | |
| 4,945,920 A | 8/1990 | Clossick | |
| 5,025,804 A | 6/1991 | Kondo | |
| 5,143,475 A | 9/1992 | Chikama | |
| 5,178,129 A * | 1/1993 | Chikama et al. | 600/142 |
| 5,290,747 A | 3/1994 | Yuo et al. | |
| 5,300,087 A | 4/1994 | Knoepfler | |
| 5,330,502 A | 7/1994 | Hassler et al. | |
| 5,454,827 A | 10/1995 | Aust et al. | |
| 5,507,773 A | 4/1996 | Huitema et al. | |
| 5,540,706 A | 7/1996 | Aust et al. | |
| 5,549,637 A | 8/1996 | Crainich | |
| 5,569,270 A | 10/1996 | Weng | |
| 5,618,294 A | 4/1997 | Aust et al. | |
| 5,649,955 A | 7/1997 | Hashimoto et al. | |
| 5,766,196 A | 6/1998 | Griffiths | |
| 5,851,212 A | 12/1998 | Zirps et al. | |
| 5,860,995 A | 1/1999 | Berkelaar | |
| 5,885,288 A | 3/1999 | Aust et al. | |
| 5,899,914 A | 5/1999 | Zirps et al. | |
| 5,919,199 A | 7/1999 | Mers Kelly et al. | |

(Continued)

FOREIGN PATENT DOCUMENTS

DE 41 36 861.4 5/1993

*Primary Examiner*—Beverly M. Flanagan
(74) *Attorney, Agent, or Firm*—Myers Dawes Andras & Sherman LLP; Joseph C. Andras (57) ABSTRACT

An articulating shaft includes an outer tubular member having a longitudinal axis and portions defining a slot. An inner tubular member is disposed within the outer member and movable about the axis of the outer member. A wedge carried by the inner member is movable within the slot in an interference fit with the slot portions to articulate the outer member. In an associated method, the inner member can be turned in a first direction to bend the outer member in an associated second direction, and the inner member can be turned in a third direction to move the outer member in an associated fourth direction.

19 Claims, 6 Drawing Sheets

U.S. PATENT DOCUMENTS

| | | | |
|---|---|---|---|
| 5,921,956 A * | 7/1999 | Grinberg et al. | 604/95.01 |
| 5,938,678 A | 8/1999 | Zirps et al. | |
| 5,957,964 A * | 9/1999 | Ceravolo | 607/109 |
| 6,048,339 A | 4/2000 | Zirps et al. | |
| 6,053,907 A | 4/2000 | Zirps | |
| 6,077,287 A | 6/2000 | Taylor et al. | |
| 6,491,626 B1 * | 12/2002 | Stone et al. | 600/141 |
| 2003/0176874 A1 | 9/2003 | Sauer | |
| 2004/0122449 A1 | 6/2004 | Modesitt et al. | |
| 2004/0167547 A1 | 8/2004 | Beane et al. | |

* cited by examiner

ARTICULATING SHAFT

CROSS REFERENCE TO RELATED APPLICATIONS

This is a non-provisional application claiming the benefit of U.S. Provisional Patent Application Ser. No. 60/460,487, filed on Apr. 3, 2003, and entitled Articulating Shaft, which is fully incorporated herein by reference.

BACKGROUND OF THE INVENTION

1. Field of the Invention

This invention relates generally to surgical instruments and more specifically to instruments having flexible or articulating shafts.

2. Description of the Prior Art

Surgical instruments, particularly those used in arthroscopic surgery, commonly are constructed with a shaft having a proximal end and a distal end. Some of these instruments have flexible shafts which permit them to be bent into a desired configuration. In most of these cases, the proximal end of a shaft is operable to articulate the distal end of the shaft.

By way of example, it will be noted that in many arthroscopic surgeries it is necessary to introduce a forceps or some other instrument through a straight cannula. Once the tip of the instrument is inside the body it may be desirable to force a curve into the distal end so that the tip can cut, grab or perform some other function from a perspective not possible with a straight approach. Many instruments have a bend permanently set in the distal end; in order to accommodate such an instrument, a straight cannula with a very large diameter has been required.

BRIEF SUMMARY OF THE INVENTION

In accordance with at least one embodiment of the present invention, a flexible shaft is provided which can be controlled at the proximal end to flex or articulate the shaft at the distal end. It is of particular advantage that the shaft can be locked in the desired shape so that it maintains the shape while accommodating aggressive cutting or grabbing of the tissue. In one aspect of the invention, an articulating shaft has a distal end that is bendable by operation of a proximal end of the shaft. An outer member having an axis extending from the proximal end to the distal end is provided in the form of an outer tube. An inner tube is disposed within the outer tube. Portions of one of the inner tube and the outer tube define a slot having a first end and a second end wider then the first end. A wedge is carried by the other of the inner tube and the outer tube and is movable within the slot between the first end of the slot and the second end of the slot. The outer tube and the inner tube are operable at the proximal end to move the wedge within the slot toward the first end of the slot. This movement bends the tubes and articulates the distal end of the shaft.

In one aspect of the invention, an articulating shaft with a proximal end and a distal end is bendable at the distal end by operation of the proximal end. The shaft includes an outer member having an axis extending from the proximal end to the distal end, the outer member having a configuration of a tube with a first longitudinal side and a second longitudinal side Portions of the first longitudinal side define a slot having a first end and a second end wider than the first end. An inner member is disposed within the outer member and carries a wedge that is movable within the slot between the first end of the slot and the second end of the slot. The inner member is operable at the proximal end of the shaft to move the wedge within the slot and toward the first end of the slot. This movement bends the outer tube away from the first longitudinal side and toward the second longitudinal side of the outer member.

In another aspect of the invention, an outer tubular member has a longitudinal axis and portions defining a slot. An inner member is disposed within the outer member and movable about the axis of the outer member. A wedge is carried by the inner member and movable within the slot in an interference fit with the slot portions to bend the outer member.

In another aspect of the invention, the inner member is disposed within the outer member and movable with a turn of a particular distance and a particular direction to produce in the outer member a bend having a magnitude and direction. The magnitude of the bend is dependent on the particular distance of the turn, and the direction of the bend is dependent upon the particular direction of the turn.

In still a further aspect, the invention includes a method wherein an outer member is provided with a slot and an inner member is provided with a wedge. The inner member is mounted within the outer member with the wedge disposed in the slot. The outer member is bent in a first direction by turning the inner member in a second direction, while the outer member is bent in a third direction opposite to the first direction by turning the inner member in a fourth direction opposite to the second direction.

These and other features and advantages of the invention will become more apparent with a description of preferred embodiments and reference to the associated drawings.

DETAILED DESCRIPTION OF THE PREFERRED EMBODIMENTS

Figure 1:
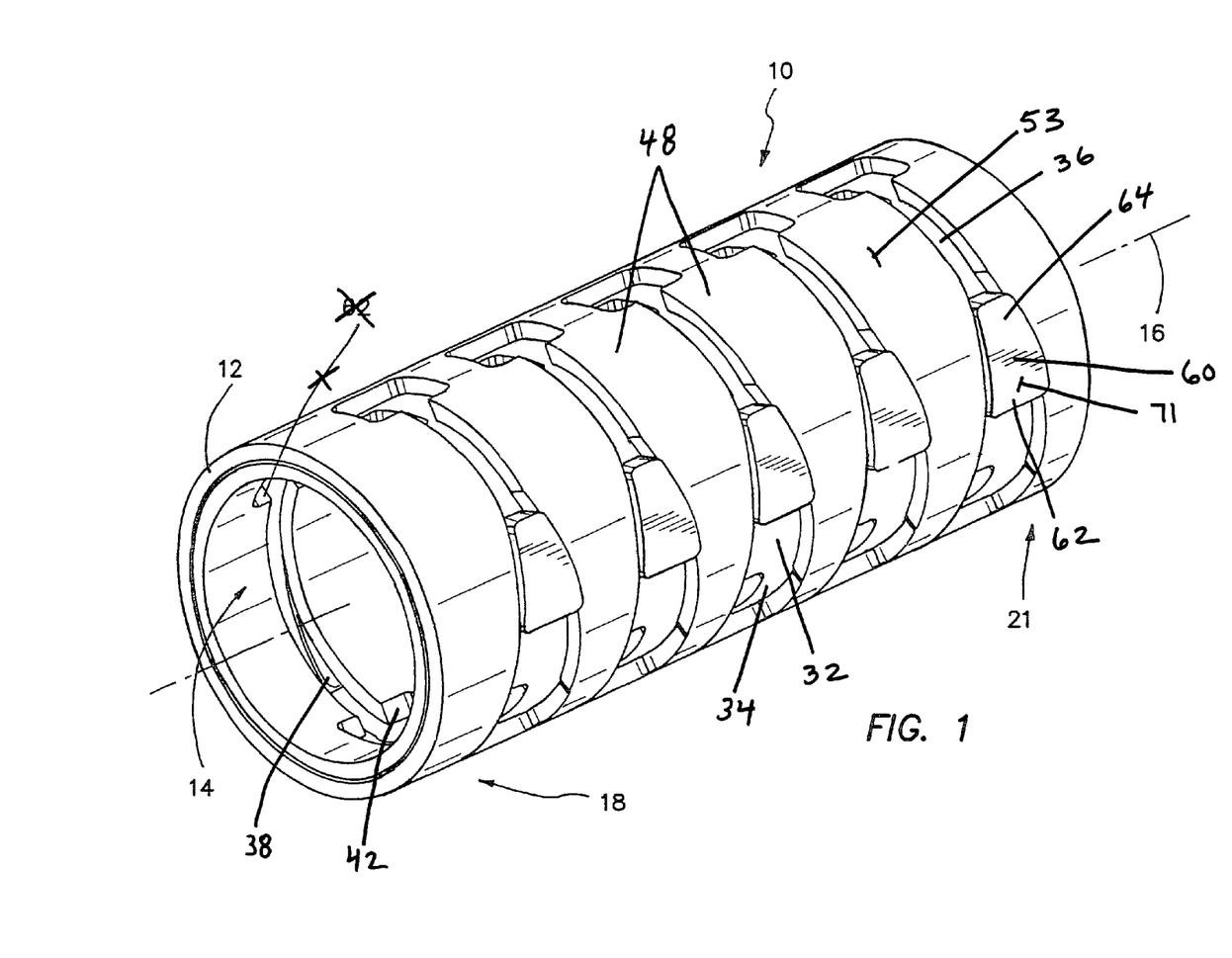
FIG. 1 is a perspective view of one embodiment of the articulating shaft of the present invention.

A flexible or articulating shaft is illustrated in FIG. 1 and designated by the reference numeral 10. In this embodiment, the shaft 10 includes an outer tube 12 and a coaxial inner tube 14 that are circumferentially moveable with respect to each other. The tubes 12 and 14 are disposed on a common axis 16, which extends between a proximal end 18 and a distal end 21.

Figures 2, 3:
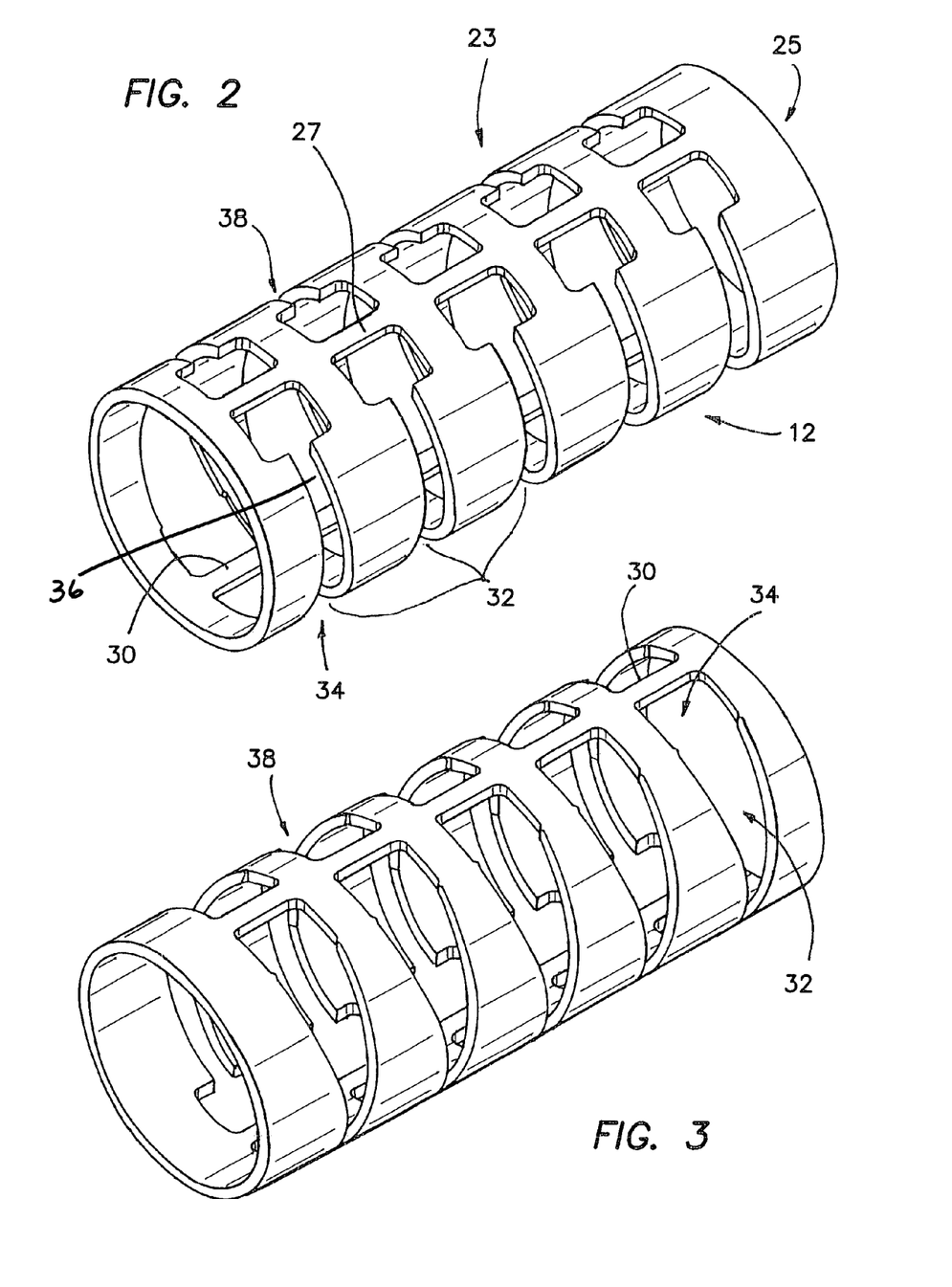
FIG. 2 is a perspective view of an outer tube illustrating the narrow end of slots formed in one longitudinal side of the tube.
FIG. 3 is a perspective view of the outer tube showing a wide end of the slots formed in a second longitudinal side of the outer tube.
Figure 4:
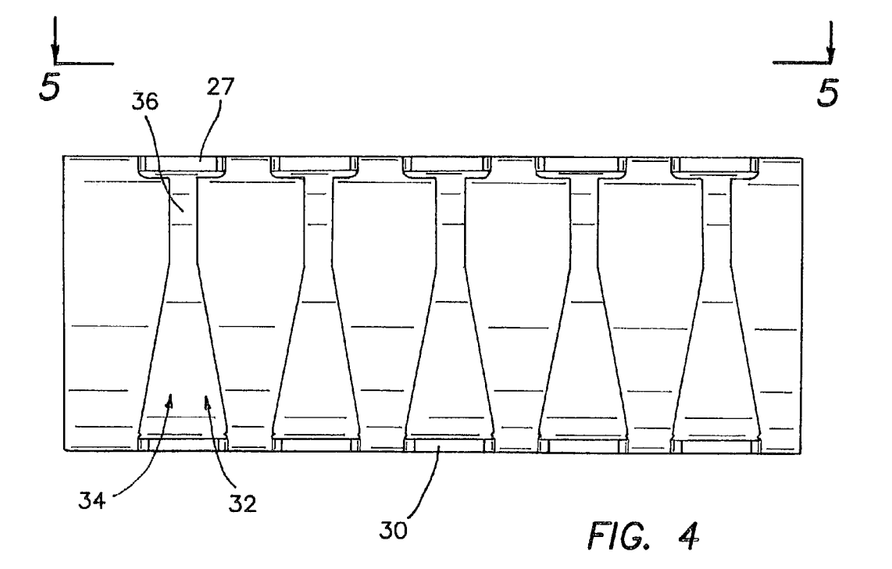
FIG. 4 is a side elevation view showing the individual slots with a narrow end and a wide end.
Figure 5:
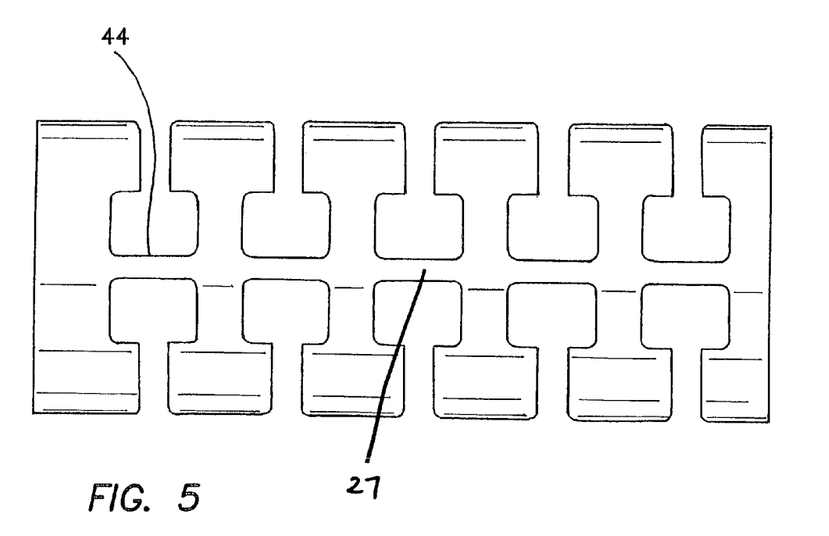
FIG. 5 is a top plan view illustrating a web disposed between the narrow ends of the opposed slots.

The outer tube 12 of this embodiment is illustrated in the perspective view of FIG. 2. In this view, it can be seen in the outer tube 12 has a pair of longitudinal sides 23 and 25 that are separated by a pair of webs 27 and 30. A plurality of slots 32 are formed in the longitudinal side 25 and configured to extend circumferentially from a large end 34 to a narrow end 36. Similar slots 38 are formed in the longitudinal side 23. These slots 38 are formed as a mirror image of the slots 32 so that the narrow ends of the slots 32 and 38 are disposed in proximity to the web 27, and the wide areas 34 of the slots 32 and 38 are formed in proximity to the web 30. The outer tube 12 is rotated 180 degrees in the perspective view of FIG. 3 in order to better illustrate the wide end 34 of the slots 32 and 38 and the associated web 30. A side elevation view showing the full length of the slots 32 is illustrated in FIG. 4, while the web 27 is best shown in the top plan view of FIG. 5.

Figures 6, 7:
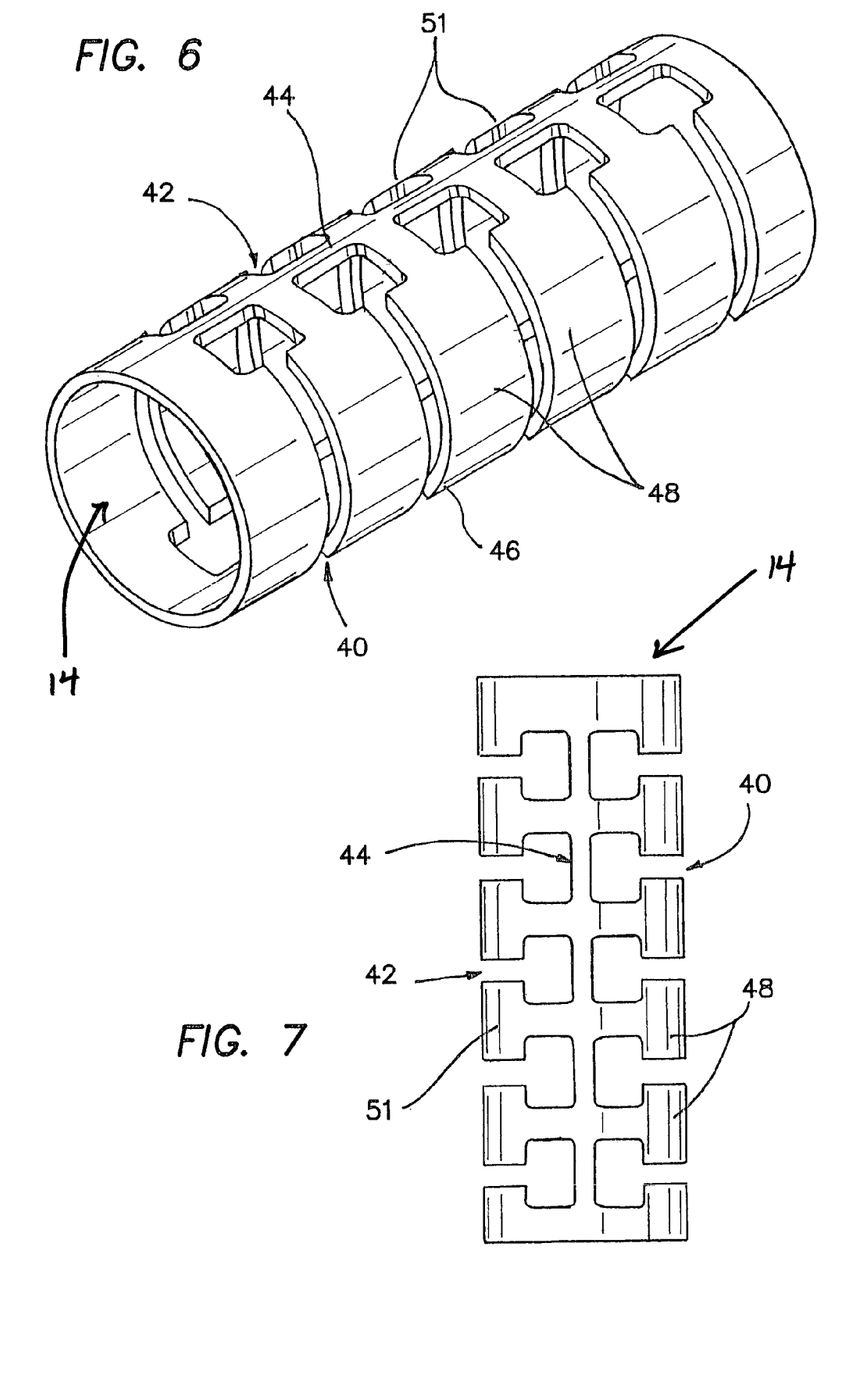
FIG. 6 is a perspective view illustrating an inner tube in the embodiment of FIG. 1.
FIG. 7 is a top plan view of the inner tube illustrating a web and bend stops associated with the slots.

A preferred embodiment of the inner tube 14 is illustrated in the prospective view of FIG. 6. This inner tube 14 also has slots 40 and 42 which are disposed on opposing sides of webs 44 and 46. In the illustrated embodiment, the slots 40 and 42 are similar in shape and have a generally constant width along their circumferential length.

The slots 40 are defined by adjacent wedge pads 48 which extend circumferentially between the webs 44 and 46. Similar wedge pads 51 define the opposing slots 42 which extend circumferentially between the webs 44 and 46. A top plan view illustrated in FIG. 7 best shows the web 44 disposed between the slots 40 and 42. From this view it can be appreciated that when the inner tube 14 is bent or articulated to the right in FIG. 7, the slots 40 close and form bend stops which inhibit overbending of the inner tube 14. Similarly, if the inner tube 14 is bent to the left in FIG. 7, the slots 42 function as bend slots inhibiting overbending of the tube 14.

Figure 8:
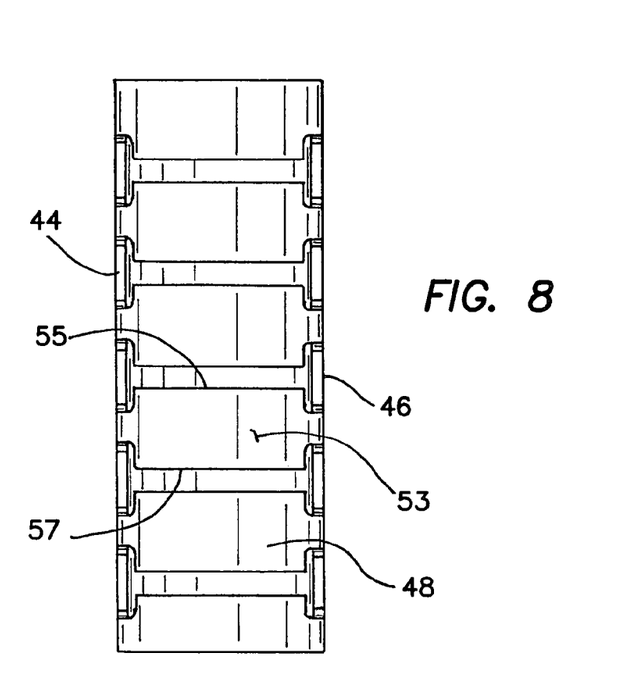
FIG. 8 is a wedge pads associated with the embodiment of FIG. 1.
Figures 9, 10, 11:
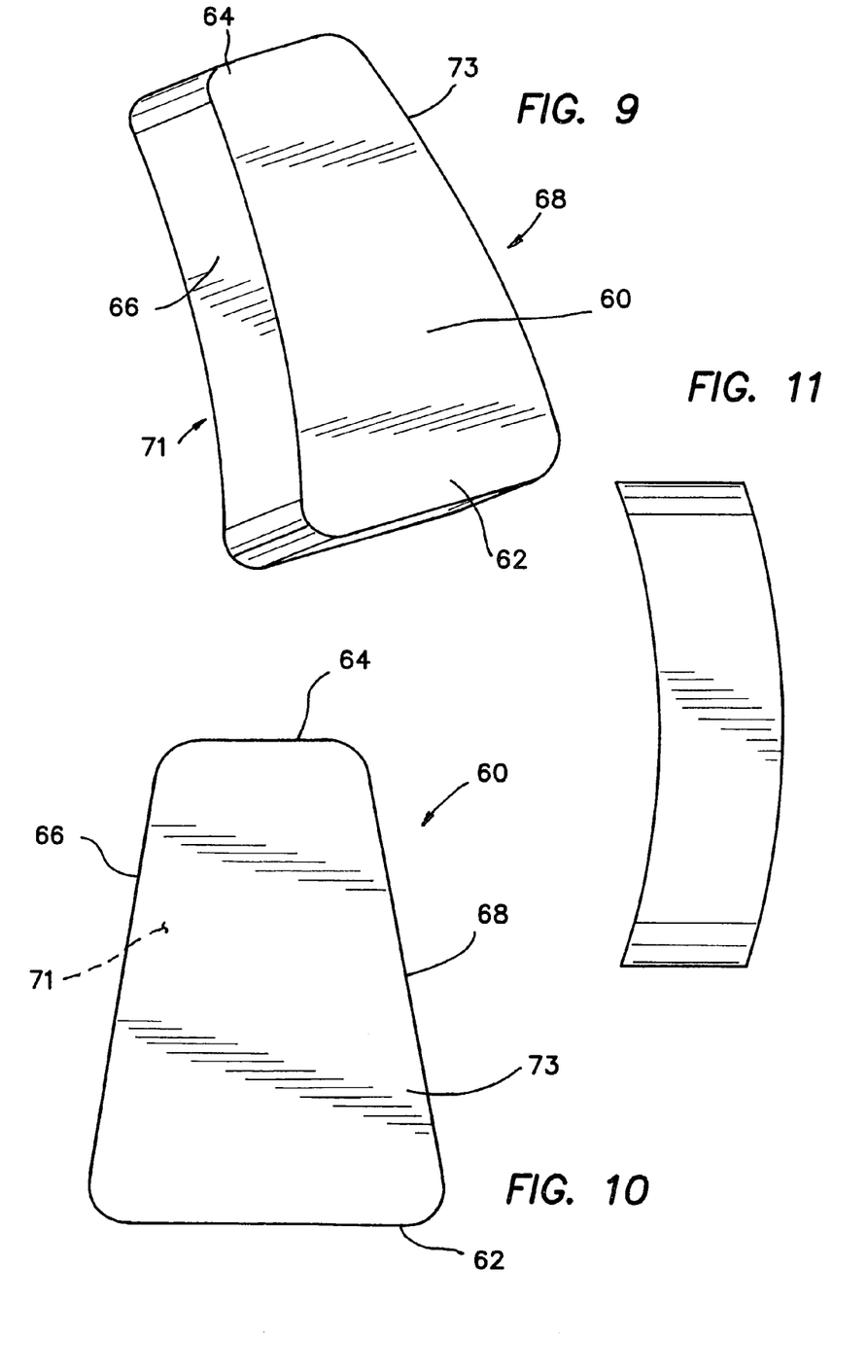
FIG. 9 is a perspective view of a wedge carried on a wedge pad of the inner tube.
FIG. 10 is a top plan view of the wedge.
FIG. 11 is a side elevation view of the wedge.
Figure 12:
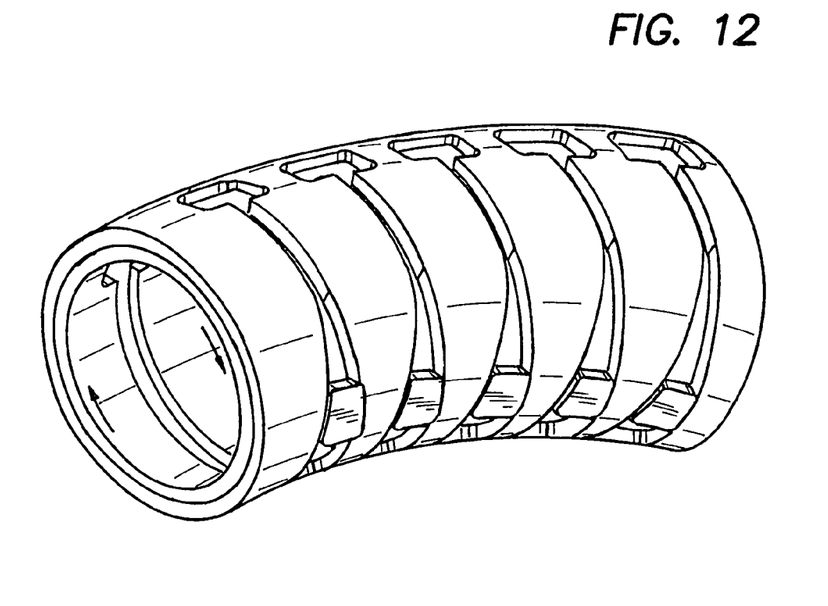
FIG. 12 is a perspective view of a bent shaft.

A plurality of wedge pads 48, best illustrated in the side view of FIG. 8, provide substrates for the attachment of wedges 60, best illustrated in FIG. 9. In this embodiment, the wedge pads 48 are each provided with a cylindrical surface 53 that is bounded by radial surfaces 55 and 57. It is these cylindrical surfaces 53 of the wedge pads 48 which are configured to receive the wedges 60. These wedges 60 can be adhered, welded, machined or otherwise disposed in a fixed relationship with an associated one of the cylindrical surfaces 53. In a preferred embodiment, best illustrated in FIG. 9, the wedge 60 has a broad end 62 and a narrow end 64 with side surfaces 66 and 68 which extend between a concave surface 71 and a convex surface 73. These elements are also illustrated in the top plan view of FIG. 10. Of course, the wedges 60, may have other than a triangular configuration; for example, a round pin may be of particular advantage in a different embodiment.

With further reference to FIG. 1, it can be seen that when operatively disposed, the wedges 60 are mounted with the concave surface 71 fixed to the cylindrical surface 53 of the wedge pad 48. In a preferred embodiment, the wedges 60 are mirrored. Importantly, the wedges 60 are mounted within respected slots 32, with the broad end 62 of the wedge 60 facing the wide end 34 of the slot 32 and the narrow end 64 of the wedge 60 facing the narrow end 36 of the slot 32. Other wedges 60 are similarly disposed on the opposite side of the shaft 10 and oriented as a mirror image of the wedges 60 in the slots 42.

In operation, the inner tube 14 can be rotated relative to the outer tube 12 to move the wedges 60 within their respective slots 32 and 42. When the inner tube is turned counterclockwise with respect to the outer tube 14, the wedges 60 move toward the narrow end 36 of the slots 32, upwardly in FIG. 1. As this movement occurs, the wedges 60 tend to separate the walls defining the slots 32. As a result, the side of the tube 12 which has the slots 32 and the wedges 60, tends to elongate. This same counterclockwise rotation moves the wedges 60 downwardly toward the broad end of the slots 42. This permits the side of the tube 12 having the slots 42 and wedges 60 to contract. This opposing expansion and contraction articulates the outer tube 12 as well as the inner tube 14 so that the entire shaft 10 tends to bend away from the slots 32 and towards the slots 38. It will be noted that the direction the inner tube 14 is turned is an angular direction, while the direction the outer tube 12 is bent is a linear direction.

The opposite effect is achieved when the inner tube 14 is rotated clockwise with respect to the outer tube 12. In this case, the wedges 60 move toward the narrow end of their slots 42 causing those slots to expand and the associated side of the tube 12 to elongate. The wedges 60 are moved toward the wider end of their slots 32 to permit contraction of their side of the tube 12. As a result, the shaft 10 tends to articulate away from the slots 38 and towards the slots 32. This articulation of the distal end 21 of the shaft 10 is accomplished merely by rotating the tubes 12 and 14 relative to each other at the proximal end 18 to the shaft 10.

In will be appreciated that in another embodiment of the invention, the tubes 12 and 14 could be switched. In such an embodiment, the wedges 60 would be carried on an inner surface of the outer tube and would be moveable within radial slots created in the inner tube.

In another embodiment, the wedges 60 could be replaced generally with any structure moveable within radial slots to alternatively expand and contract these slots on opposing sides of the shaft. As an example and not by way of limitation, the wedges 60 may be replaced with round pins, for instance.

One advantage associated with the present invention relates to the tendency of the wedges 60 to remain at any given point within the associated slots 32, 34 until the tubes 12 and 14 are again actively rotated relative to each other. This locking feature of the associated embodiment, is achieved by the frictional resistance encountered between the wedges 60 and the associated sides of their respective slots 32 and 38. The locking feature can be further enhanced by adding frictional resistance in the form of detents located on the proximal control sections. In general, the locking feature permits the surgeon to articulate the shaft to a particular curve configuration and to know that the shaft 10 will retain that degree of curvature until it is changed by the surgeon.

These features collectively permit the surgeon to introduce the shaft 10 through a small diameter straight cannula and then to operate the shaft 10 at the proximal end 18 to articulate the distal end 21. When the desired degree of articulation is achieved, the relative rotation of the tubes 12 and 14 can be stopped and the locking feature relied on to maintain the desired bend through aggressive cutting and/or grabbing of the tissue.

Thus, these and other modifications and additions will be obvious to those skilled in the art and may be implemented to adapt the present invention for use in a variety of different applications.

The invention claimed is:

1. An articulating shaft having a proximal end and a distal end, the distal end being bendable by operation of the proximal end, comprising:
an outer member having an axis extending from the proximal end to the distal end, the outer member having a configuration of a tube with a first longitudinal side and a second longitudinal side;
portions of the first longitudinal side define a slot having a first end and a second end wider than the first end;
an inner member disposed within the outer member;
a wedge carried by the inner member and movable within the slot between the first end of the slot and the second end of the slot;
the inner member being operable at the proximal end to move the wedge within the slot and toward the first end of the slot, to bend the outer tube away from the first longitudinal side and toward the second longitudinal side.

2. The articulating shaft recited in claim 1, wherein the slot is defined generally radially of the outer member.

3. The articulating shaft recited in claim 1, wherein the slot is a first slot and the wedge is a first wedge, and the shaft further comprises:
portions of the second longitudinal side defining a second slot having a first end and a second end wider than the first end;
a second wedge carried by the inner member and movable within the second slot between the first end of the second slot and the second end of the second slot; and
the inner member being operable at the proximal end to move the second wedge within the second slot and toward the first end of the second slot, to bend the outer tube away from the second longitudinal side and toward the first longitudinal side.

4. The articulating shaft recited in claim 1, wherein:
the tube is a first tube; and
the inner member has a configuration of the second tube.

5. The articulating shaft recited in claim 4, wherein the first tube is coaxial with the second tube.

6. The articulating shaft recited in claim 3, wherein the second slot is a mirror image of the first slot.

7. The articulating shaft recited in claim 3, further comprising:
a first web disposed between the first end of the first slot and the first end of the second slot; and
a second web disposed between the second end of the first slot and the second end of the second slot.

8. The articulating shaft recited in claim 1 wherein the inner member is rotatable relative to the outer member to move the wedge between the first end of the first slot and the second end of the first slot.

9. An articulating shaft having a proximal end a distal end, the distal end being bendable by operation of the proximal end, the shaft comprising:
an outer tubular member having a longitudinal axis;
an inner tubular member disposed within the outer member and movable about the axis of the outer member;
one of the inner tubular member and outer tubular member including portions defining a slot; and
a wedge carried by the other of the inner tubular member and the outer tubular member, the wedge being movable within the slot in an interference fit with the slot portions to bend the outer member in a direction.

10. The articulating shaft recited in claim 9, wherein:
the slot portions are oriented generally radially of the axis; and
at least one of the inner tubular member and the outer tubular member is movable by rotation about the axis.

11. The articulating shaft recited in claim 9 wherein the portions of the one tubular member are first portions, the slot is a first slot, the wedge is a first wedge, and the direction is a first direction, and the shaft further comprising:
second portions defining a second slot opposing the first slot in the one tubular member; and
a second wedge carried by the other tubular member, the second wedge being movable within the second slot to bend the outer tube in a second direction different than the first direction.

12. The articulating shaft recited in claim 9, wherein:
the slot has a first end and a second end; and
the first end of the slot has a first width and the second end of the slot has a second width greater than the first width.

13. The articulating shaft recited in claim 9, wherein:
the slot is a first slot;
the inner member includes a pair of wedge pads separated by a second slot having a width; and
the magnitude of the bend is dependent on the width of the second slot.

14. A method for articulating a shaft having a longitudinal configuration with a proximal end and a distal end, the method including the steps of:
providing a first member with a slot;
providing a second member with a wedge;
mounting the second member relative to the first member with the wedge disposed in the slot;
turning the second member relative to the first member in a first direction to bend the first member in a second direction; and
turning the second member relative to the first member in a third direction to bend the first member in a fourth direction.

15. The method recited in claim 14 wherein the first direction and the third direction are angular directions, and the second direction and the fourth direction are linear directions.

16. The method recited in claim 15 wherein the third direction is opposite to the first direction and the fourth direction is opposite to the second direction.

17. The method recited in claim 16 wherein the wedge is movable in an interference fit with the portions defining the slot.

18. An articulating shaft having a proximal end and a distal end, comprising:
a first member movable with one of a slot pattern and a wedge mechanism;
a second member movable with the other of the slot pattern and the wedge mechanism; and
the wedge mechanism being movable in the slot pattern by operation of the proximal end of the shaft to bend the distal end of the shaft.

19. The articulating shaft recited in claim 18, wherein:
the slot pattern includes a pair of opposing slots; and
the wedge mechanism includes a pair of opposing wedges each associated with one of the opposing slots.

* * * * *